United States Patent
Drake, Jr. et al.

(10) Patent No.: US 8,064,488 B2
(45) Date of Patent: Nov. 22, 2011

(54) MID-IR LASER FOR GENERATION OF ULTRASOUND

(75) Inventors: Thomas E. Drake, Jr., Fort Worth, TX (US); Marc Dubois, Keller, TX (US); Peter W. Lorraine, Niskayuna, NY (US); John B. Deaton, Jr., Niskayuna, NY (US); Robert Filkins, Niskayuna, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 12/120,949

(22) Filed: May 15, 2008

(65) Prior Publication Data

US 2009/0285244 A1    Nov. 19, 2009

(51) Int. Cl.
  *H01S 3/30*    (2006.01)
(52) U.S. Cl. ............... 372/4; 372/21; 372/69; 702/159
(58) Field of Classification Search ............... 372/4, 21, 372/69; 702/159
See application file for complete search history.

(56) References Cited

U.S. PATENT DOCUMENTS

| | | | |
|---|---|---|---|
| 7,286,241 B2 | 10/2007 | Drake, Jr. | |
| 7,370,532 B2 | 5/2008 | Osterkamp | |
| 7,463,363 B2 | 12/2008 | Drake, Jr. | |
| 2002/0009115 A1* | 1/2002 | Sumiyoshi et al. | 372/75 |
| 2006/0215174 A1* | 9/2006 | Dubois et al. | 356/502 |
| 2009/0010285 A1* | 1/2009 | Dubois et al. | 372/3 |

OTHER PUBLICATIONS

Dubois et al., "Experimental verification of the effects of optical wavelength on the amplitude of laser generated ultrasound in polymer-matrix composites", Ultrasonics 40 (2002), pp. 809-812.
Dubois et al., "Experimental comparison between optical spectroscopy and laser-ultrasound generation in polymer-matrix composites", Applied Physics Letter, vol. 79, No. 12, Sep. 17, 2001, pp. 1813-1815.
Dubois et al., "Progress on the Development of an Advanced Laser Ultrasound Generation Source for Inspecting Polymer-Matrix Composites", CP615, Review of Quantitative Nondestructive Evaluation vol. 21, ed. by D.O. Thompson and D. E. Chimenti, American Institute of Physics (2002), pp. 300-307.
"Efficient Mid-Infrared Laser Using 1.9 um-Pumped Ho:YAG and ZnGeP2 Optical Parametric Oscillators" Journal of the Optical Society of America, Budni, P.A., et al, 2000.
"Midinfrared Laser Source with High Power and Beam Quality", Applied Optics, Lippert, E., et al, 2005.
"Laser Ultrasonic Technology in Europe for Innovative Inspection of Aircraft Structures", World Conference on NDT, Guilliorit, E., et al, 2004.

* cited by examiner

*Primary Examiner* — Tod T Van Roy
(74) *Attorney, Agent, or Firm* — Bracewell & Giuliani LLP

(57) ABSTRACT

A compact high average power mid infrared range laser for ultrasound inspection. The laser comprises one of a Nd:YAG or Yb:YAG laser pumped by a diode at 808 nm to produce a 1 micron output beam. The 1 micron output beam is directed to an optical parametric oscillator where the beam wavelength is converted to 1.94 microns and conveyed to a mid infrared emission head. The emission head comprises one of a Ho:YAG or Ho:YLG laser optically coupled with a second optical parametric oscillator. The second optical parametric oscillator forms a generation output beam for creating ultrasonic displacements on a target. The generation output beam wavelength ranges from about 3 to about 4 microns, and can be 3.2 microns.

13 Claims, 3 Drawing Sheets

MID-IR LASER FOR GENERATION OF ULTRASOUND

BACKGROUND

1. Field of Invention

The invention relates generally to the field of non-destructive testing. More specifically, the present invention relates to a system to create a mid-range infrared generation laser beam.

2. Description of Prior Art

Recent developments in creating composite materials have expanded the use of composite materials into a wide variety of applications. Because of its high strength and durability combined with its low weight, composites are replacing metals and metal alloys as the base material for certain load bearing components. For example, composites are now commonly used as a material for body parts and structure in vehicles such as automobiles, watercraft, and aircraft. However, to ensure composite mechanical integrity, strict inspections are required. The inspections are typically required upon fabrication of a component made from a composite and periodically during the life of the component.

Laser ultrasound is one example of a method of inspecting objects made from composite materials. The method involves producing ultrasonic vibrations on a composite surface by radiating a portion of the composite with a pulsed generation laser. A detection laser beam is directed at the vibrating surface and scattered, reflected, and phase modulated by the surface vibrations to produce phase modulated light. Collection optics receives the phase modulated laser light and directs it for processing. Processing is typically performed by an interferometer coupled to the collection optics. Information concerning the composite can be ascertained from the phase modulated light processing, the information includes the detection of cracks, delaminations, porosity, foreign materials (inclusions), disbonds, and fiber information.

FIG. 1 provides one prior art example of a laser system 10 for producing a pulsed generation laser beam. The laser system 10 is configured to produce laser light in the mid infrared range and comprises a mid infrared laser head 11 optically coupled to a mid infrared emission head 30. The mid IR laser head 11 includes a thulium yttrium lithium fluoride (Th:YLF) end pumped by a pair of diode pumps (16, 18). The output 19 of diode pump 18 pumps one end of the Th:YLF laser 20, the other end of the laser 20 is pumped by pump diode 16. Pump diode 16 output beam (not shown) passes through the transmissible side of a dichroic mixer 24 and into the lower end of the laser 20. The thulium laser output 20 is directed towards the reflective side of the dichroic mixer 24 and is reflected towards the emission head 30. Optional input and output couplers (21, 25) are provided on the respective input and output of the thulium laser 20. In this prior art embodiment, the pump diodes (16, 18) pump the thulium laser 20 at a wavelength of 794 nanometers. The thulium output beam 22 operates at approximately 1.94 microns.

The emission head 30 has a holmium yttrium aluminum garnet (Ho:YAG) laser 34 operatively coupled with a frequency converter 38. The frequency converter 38 is depicted as an optical parametric oscillator (OPO). The Ho:YAG laser 34 receives the reflected laser output 26 at a wavelength of approximately 1.94 microns and emits its corresponding output beam 36 at a wavelength of about 2.05 microns. The OPO converts the output beam 36 to a signal beam and an input beam, where the signal beam has a wavelength of about 3.2 microns and the idler beam has a wavelength of about 5.7 microns.

The laser system 10 emits from about five to about ten watts of 3 to 4 micron light, but requires about 1 kilowatt in power of pump diodes. Accordingly, the mid IR laser head 11 is equipped with an associated cooling circuit 14 and power supply 12 that requires a substantial capacity to support laser system 10 operation. The increased power in cooling capacity for the system 10 results in a large volume and a large mass laser head. Additionally, the 794 nanometer pump diodes are not common readily available items. Typically the Ho:YAG laser output is at about 2.05 microns where it is converted within the OPO to a mid IR laser output of about 3.2 microns. A Q-switching device (not shown) is typically included within the emission head 30. Q-switching provides pulsing to the output laser beam 40 for creating the thermo-elastic displacements on a target surface that then forms ultrasonic displacements on the target surface. The Ho:YAG laser 34 is shown with an input coupler 32 at its input and an output coupler 33 at its output. The OPO 38 is illustrated having both an input and output coupler (35, 37).

SUMMARY OF INVENTION

Disclosed herein is a mid infrared range laser system for ultrasonic testing comprising a yttrium aluminum garnet (YAG) laser having an output beam, a pump diode operatively coupled to the YAG laser, an optical frequency converter operatively coupled to the YAG laser output beam and having an output beam, where the optical frequency converter output beam wavelength is about 2 microns, and a laser system output beam directed at an ultrasonic testing target. The YAG laser may be a neodymium yttrium aluminum garnet (Nd:YAG) laser or a ytterbium-doped yttrium aluminum garnet (Yb:YAG) laser. The optical frequency converter may be an optical parametric oscillator and the pump diode beam output may have a wavelength of about 808 nanometers. The optical frequency converter output beam can be about 1.94 microns. The mid infrared range laser system may also include an emission head coupled to the optical frequency converter output beam, where the emission head includes an output beam having a wavelength in the mid infrared spectral range, and where the emission head output beam forms the laser system output beam. The emission head output beam wavelength can be about 3.2 microns and may include a laser device, the laser device coupled to receive the optical frequency converter output beam, and a second optical frequency converter, the laser device having an output directed to the second optical frequency converter. The laser device of the emission head may be one of a holmium yttrium lithium fluoride laser or a holmium yttrium aluminum garnet laser. The second optical frequency converter may be an optical parametric oscillator.

Also disclosed herein is a system for ultrasonic analysis of a test object comprising, a laser head pumped with a laser beam having a wavelength of about 808 nanometers and having a laser head output beam having a wavelength of about 2 microns, and a mid infrared range emission head configured to receive the laser head output beam and emit a generation output beam in the mid infrared wavelength range, wherein the generation output beam is directed at the test object to create thermo-elastic expansion thereon and form ultrasonic displacements. The generation output beam wavelength may be about 3.2 microns. The laser head can be an yttrium aluminum garnet laser having an output beam having a wavelength of about 1 micron and may be one of a neodymium yttrium aluminum garnet laser or a ytterbium-doped yttrium aluminum garnet laser. The laser head may include an optical parametric oscillator configured to receive the yttrium aluminum garnet laser output beam and emit a converted beam that forms the laser head output beam. The mid infrared range emission head has a laser device having a laser output beam with a wavelength of about 2.05 microns, and an optical parametric oscillator configured to receive the laser output beam and emit a converted beam, wherein the converted beam forms the generation output beam. The laser device can be a holmium yttrium lithium fluoride laser or a holmium yttrium aluminum garnet laser. An optical fiber may be used to couple the pump head and emission head.

BRIEF DESCRIPTION OF DRAWINGS

Some of the features and benefits of the present invention having been stated, others will become apparent as the description proceeds when taken in conjunction with the accompanying drawings, in which.

Figure 1:
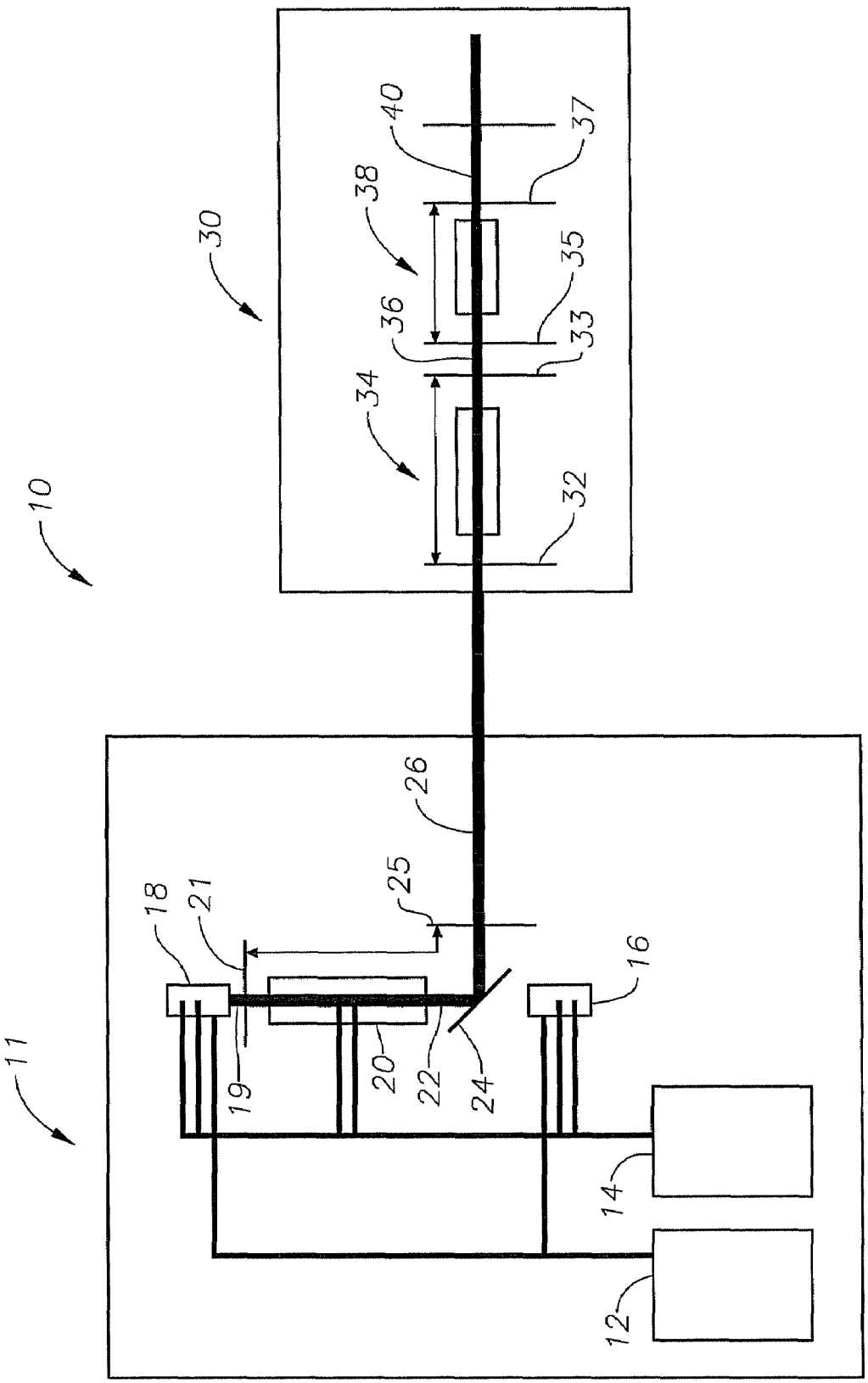
FIG. 1 is a schematic view of a prior art ultrasonic laser source.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout. For the convenience in referring to the accompanying figures, directional terms are used for reference and illustration only. For example, the directional terms such as "upper", "lower", "above", "below", and the like are being used to illustrate a relational location.

It is to be understood that the invention is not limited to the exact details of construction, operation, exact materials, or embodiments shown and described, as modifications and equivalents will be apparent to one skilled in the art. In the drawings and specification, there have been disclosed illustrative embodiments of the invention and, although specific terms are employed, they are used in a generic and descriptive sense only and not for the purpose of limitation. Accordingly, the invention is therefore to be limited only by the scope of the appended claims.

Figure 2:
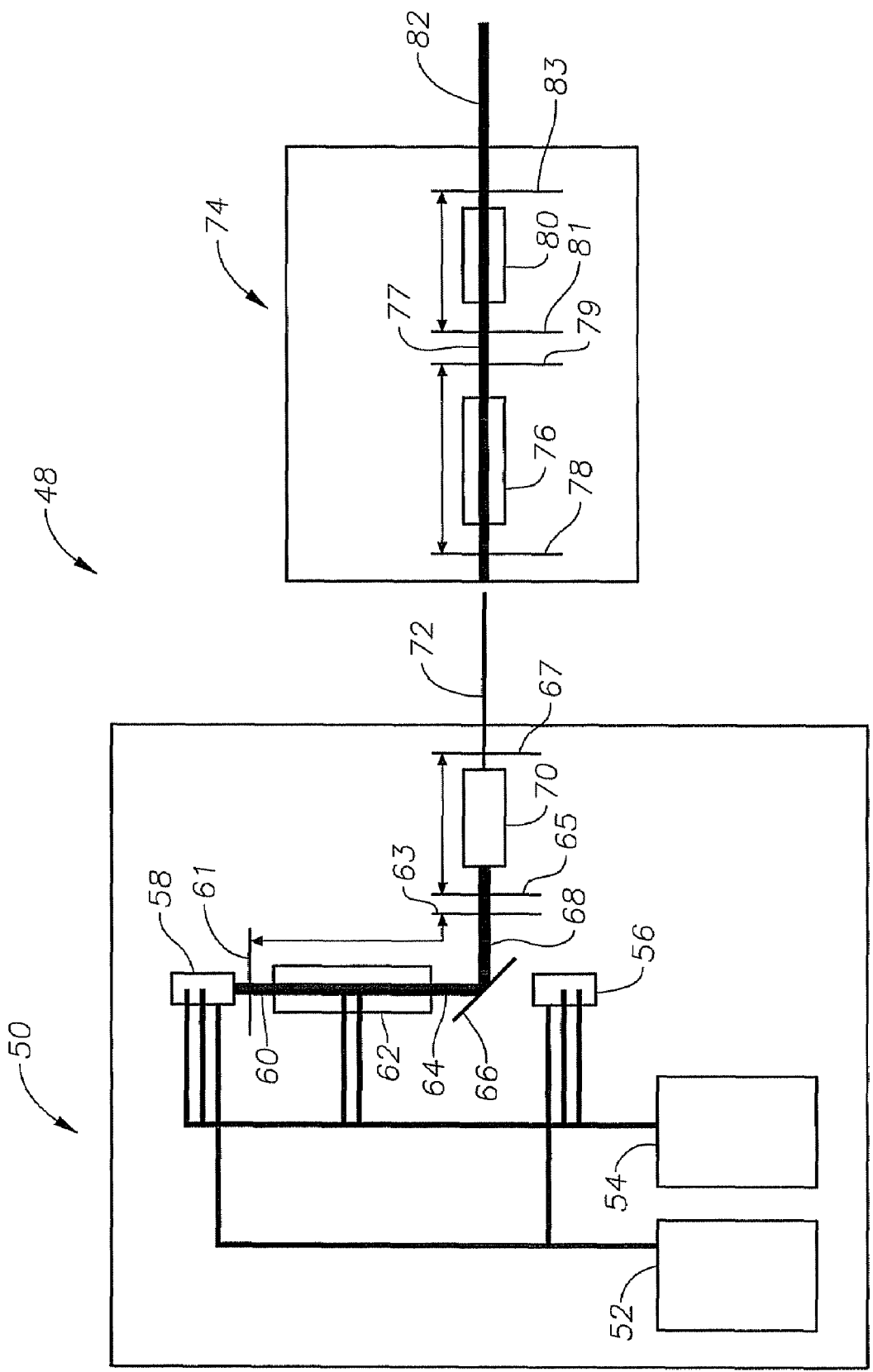
FIG. 2 is a schematic view of a mid range infrared ultrasonic laser source in accordance with the present disclosure.

With reference now to FIG. 2 depicts a schematic view of an embodiment of a mid IR laser system 48. The mid IR laser system 48 comprises a mid IR laser head 50 optically coupled to an emission head 74 via an optical fiber 72. The mid IR laser head 50 includes a yttrium aluminum garnet (YAG) laser. The YAG laser may be one of a neodymium yttrium aluminum garnet (Nd:YAG) laser or a ytterbium-doped yttrium aluminum garnet (Yb:YAG) laser. The YAG laser 62 is end pumped by a pump outlet beam 60 from a diode pump 58 on one end; on its opposite end the YAG laser 62 receives a pump outlet beam (not shown) from a pump diode 56 through the transmissive side of a dichroic mixer 66. The YAG laser 62 output 64 is optionally directed to a reflective side of the dichroic mixer 66 to form a reflected output beam 68. The reflected output beam 68 forms the optical frequency converter input 68 that is directed to the optical frequency converter 70. In one embodiment, the optical frequency converter 70 comprises an OPO. The YAG laser 62 is shown with an optional input coupler 61 and an optional output coupler 63 disposed in the path between the YAG laser 62 and the optical frequency converter 70. An input coupler 65 is shown provided at the input of the optical frequency converter 70 and a corresponding output coupler 67 is disposed at the output.

The optical frequency converter 70 receives the YAG laser 62 output and emits a converted beam that forms the emission head input beam 72. As noted above an optical fiber may provide the conduit path between the optical frequency converter 70 and the emission head 74. The emission head 74 comprises a holmium laser 76 configured to receive the emission head input beam 72. An output beam 77 from the holmium laser 76 is directed to a second optical frequency converter 80. The second optical frequency converter 80 receives the laser output beam 77 and emits a converted beam forming the mid IR laser output beam 82. The holmium laser 76 may be one of a holmium yttrium lithium fluoride (Ho:YLF) laser or a holmium yttrium aluminum garnet (Ho:YAG) laser. Optionally, the second optical frequency converter 80 may also comprise an OPO. The holmium laser 76 is illustrated in a cavity formed between an input coupler 78 and an output coupler 79. Similarly, the second optical frequency converter 80 is shown residing in a cavity between an input coupler 81 and an output coupler 83.

In one embodiment of the mid IR laser system 48 of FIG. 2, the YAG laser is pumped by the pump diodes (56, 58) where the pump laser wavelength is 808 nanometers. The YAG laser 62, in this embodiment, emits an output laser beam 64 of about 1 micron. The optical frequency converter 70 is configured to convert the approximately 1 micron output beam 64 to a converted beam having a wavelength of about 1.94 microns. In one embodiment, the holmium laser 76 further converts the beam wavelength to about 2.05 microns and the second optical frequency converter 80 emits a beam in the mid infrared range of about 3 microns to about 4 microns. The beam emitted from the second optical frequency converter forms the mid IR laser output beam 82. Optionally, the mid infrared laser output beam 82 is about 3.2 microns. More specifically, in yet another embodiment, the mid IR laser output beam 82 comprises an idler beam having a wavelength of about 5.7 microns and a signal wavelength of about 3.2 microns.

One of the many advantages of the system of FIG. 2 is the availability of pump diodes operating in the absorption band usable for the YAG laser 62. Pump diodes having an output wavelength of about 808 nanometers are more plentiful than pump diodes whose output is about 794 nanometers. Additionally, the power requirements of the mid IR laser head 50 is reduced by use of the YAG laser 62 over the mid IR laser head 11 of the thulium laser. Accordingly, the associated cooling circuit 54 size used for cooling the mid IR laser head 50 can be smaller due to the lower cooling demands. This further reduces the power requirements required from the power supply 52 to the pump diodes (56, 58). In one alternative embodiment, the YAG laser 62 may be side pumped with pump diodes thereby potentially enhancing the power efficiency of the system. Additionally, the YAG laser 62 may be powered by a single pump diode instead of the dual end pump diodes provided in FIG. 2.

Figure 3:
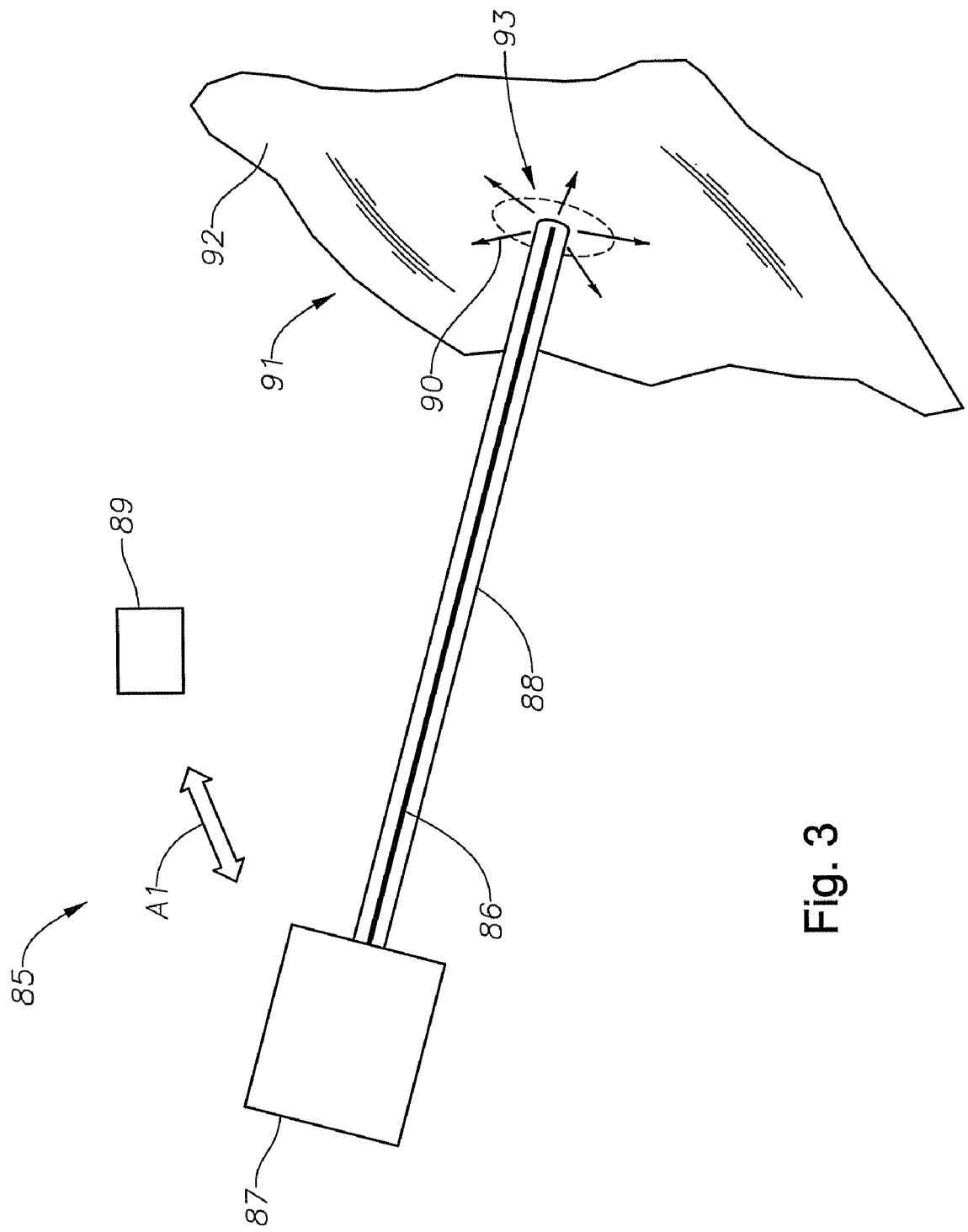
FIG. 3 is a schematic representation of a laser ultrasonic system.

FIG. 3 provides a side perspective view of one embodiment of a laser ultrasonic detection system 85. The detection system 85 comprises a laser ultrasonic unit 87 that may optionally include the mid infrared laser system 48 as described herein. The detection system 85 emits a generation beam 86 directed to an inspection target 91, where the generation beam 86 comprises the mid IR laser output beam 82 formed by the mid infrared laser system 48. The generation beam 86 contacts the inspection target 91 on an inspection surface 92. The generation beam 86 thermo-elastically expands the inspection surface 92 to produce corresponding displacements 93 on the inspection surface 92. In one embodiment, the generation beam 86 is a pulsed laser configured to produce the displacements 93 on the inspection surface 92. A detection beam 88 is also illustrated emanating from the laser ultrasonic unit 87 and is shown coaxial around the generation beam 86. Although emanating from the same laser ultrasonic unit 87, the detection and generation beams (86, 88) are generated by different sources. However, the detection beam 88 may optionally originate from a different unit as well as a different location. As is known, the detection beam 88 comprises a detection beam that is scattered, reflected, and phase modulated upon contact with the displacements 93 to form phase modulated light 90. The phase modulated light 90 from the detection beam 88 is then received by collection optics 89 and processed to determine information about the inspection target 91. The generation and detection beams (86, 88) may be scanned across the target 91 to obtain information regarding the entire surface 92. A mechanism (not shown) used to scan the beams (86, 88) may be housed within the laser ultrasonic unit 87. A processor (not shown) for controlling the mechanism and optionally for processing the data recorded by the collection optics, may also be housed in the laser ultrasonic unit 87. The collection optics 89 are shown separate from the laser ultrasonic unit 87 and in communication with the laser ultrasonic unit 87 through the arrow A, however the collection optics may be included with or within the laser ultrasonic unit 87.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A mid infrared laser system for ultrasonic testing composite material of a target, comprising:
    a laser ultrasonic unit having a generation laser source and a detection laser source mounted in the unit, the generation laser source comprising:
    an yttrium aluminum garnet (YAG) laser having an output beam with a wavelength of about 1 micron;
    a pump diode operatively coupled to the YAG laser;
    a first optical frequency converter operatively coupled to the YAG laser output beam and having an output beam, where the first optical frequency converter output beam has a wavelength of about 1.94 microns;
    a mid infrared emission head coupled to the first optical frequency converter output beam comprising a laser device and a second optical frequency converter, the laser device coupled to receive the first optical frequency converter output beam and having an output directed to the second optical frequency converter;
    an output generation beam from the second optical frequency converter comprising an idler beam having a wavelength of about 5.7 microns and a signal beam having a length of about 3.2 microns and directed at a target for creating ultrasonic thermo-elastic displacements in a surface of the target; and
    wherein the detection source generates a detection beam from the laser ultrasonic unit that is scattered upon contact with the displacements to form phase modulated light; and the system further comprises:
    collection optics that receives and processes the phase modulated light to provide data representative of the displacements.

2. The mid infrared laser system of claim 1, wherein the YAG laser comprises a laser selected from the list consisting of a neodymium yttrium aluminum garnet (Nd:YAG) laser and a ytterbium-doped yttrium aluminum garnet (Yb:YAG) laser.

3. The mid infrared laser system of claim 1, wherein the first optical frequency converter comprises an optical parametric oscillator.

4. The mid infrared laser system of claim 1, wherein the pump diode emits an optical beam whose wavelength is about 808 nanometers.

5. The mid infrared laser system of claim 1, wherein the laser device has an output beam of 2.05 microns that is directed to the second optical frequency converter.

6. The mid infrared laser system of claim 1, wherein the laser device comprises a laser selected from the list consisting of a holmium yttrium lithium fluoride (Ho:YLF) laser and a holmium yttrium aluminum garnet (Ho:YAG) laser.

7. The mid infrared laser system of claim 1, wherein the second optical frequency converter comprises an optical parametric oscillator.

8. The mid infrared laser system of claim 1, further comprising an additional pump diode for pumping the YAG laser.

9. A system for ultrasonic analysis of composite material of a test object comprising:
    a laser ultrasonic unit having a generation laser source and a detection laser source mounted in the unit, the generation laser source comprising:
    a pair of diode pumps, each having an output beam with a wavelength of about 808 nanometers;
    a YAG laser having opposite ends in operative cooperation with the output beams of the diode pumps and having an output beam with a wavelength of about 1 micron;
    a first optical parametric oscillator in operative cooperation with the output beam of the YAG laser and having an output beam with a wavelength of about 1.94 microns, a path between the YAG laser and the first optical parametric oscillator being free of any devices that would alter the shape of the beam;
    an optical fiber that receives the output beam of the first optical parametric oscillator:
    a holmium laser coupled to the optical fiber and receiving the output beam of the first optical parametric oscillator, and the holmium laser having an output beam with a wavelength of about 2.05 microns; and
    a second optical parametric oscillator in operative cooperation with the output beam of the holmium laser and having an output generation beam comprising an idler beam of about 5.7 microns wavelength and a signal beam of about 3.2 microns directed at the test object to create ultrasonic thermo-elastic displacements of the composite material thereon; wherein the detection beam source generates a detection beam that is coaxial with and surrounding the generation beam, the detection beam being scattered upon contact with the displacements to form phase modulated light; and the system further comprises:

collection optics that receive and process the phase modulated light to provide data representative of the displacements.

10. The system of claim 9, wherein the YAG laser comprises a laser selected from the list consisting of a neodyinium yttrium aluminum garnet (Nd:YAG) laser and a ytterbium-doped yttrium aluminum garnet (Yb:YAG) laser.

11. The system of claim 9, wherein the laser device is selected from the list consisting of a holmium yttrium lithium fluoride (Ho:YLF) laser and a holmium yttrium aluminum garnet (Ho:YAG) laser.

12. A method of inspecting an object made from a composite material comprising:

mounting a YAG laser, a holmium laser and a detection laser source in a laser ultrasonic unit;

pumping the YAG laser with a pump diode to emit a beam from the YAG laser having a wavelength of about 1 micron;

passing the beam for the YAG laser to an optical frequency converter without altering the shape of the beam and processing the beam from the YAG laser with the optical frequency converter to form a laser beam having a wavelength of 1.94 microns;

processing the 1.94 micron wavelength laser beam with the holmium laser and an optical parametric oscillator to form a mid infrared generation laser beam having an idler beam with a wavelength of about 5.7 microns and a signal beam having a wavelength of about 3.2 microns;

pulsing and directing the mid infrared generation laser beam from the laser ultrasonic unit to the object, creating ultrasonic thermo-elastic displacements of the composite material of the object;

directing a detection laser beam from the detection beam source in the laser ultrasonic unit at the displacements, which scatters upon contact with the displacements to form phase modulated light; and receiving with collection optics the phase modulated light and processing the phase modulated light to provide data representative of the displacements.

13. The method of claim 12, wherein the detection laser beam is coaxial with and surrounds the generation laser beam.

\* \* \* \* \*